(12) United States Patent
McDunnough et al.

(10) Patent No.: US 12,076,500 B2
(45) Date of Patent: Sep. 3, 2024

(54) SELF-INTERMITTENT URINARY CATHETER EXTENSION WITH INFECTION DETECTION, A CATHETER ASSEMBLY HAVING AN EXTENSION WITH INFECTION DETECTION AND A CATHETER ASSEMBLY HAVING INFECTION DETECTION

(71) Applicant: Advocath LLC, Fenton, MI (US)

(72) Inventors: Christine McDunnough, Fenton, MI (US); William Vickers, Holly, MI (US); William Medsker, Lawton, MI (US)

(73) Assignee: Advocath LLC, Fenton, MI (US)

( * ) Notice: Subject to any disclaimer, the term of this patent is extended or adjusted under 35 U.S.C. 154(b) by 0 days.

(21) Appl. No.: 18/244,215

(22) Filed: Sep. 8, 2023

(65) Prior Publication Data
US 2024/0108851 A1 Apr. 4, 2024

Related U.S. Application Data

(63) Continuation of application No. 17/337,350, filed on Jun. 2, 2021, now Pat. No. 11,752,299, which is a
(Continued)

(51) Int. Cl.
*A61M 25/00* (2006.01)
*A61M 39/10* (2006.01)

(52) U.S. Cl.
CPC ........ *A61M 25/0023* (2013.01); *A61M 39/10* (2013.01); *A61M 2202/0439* (2013.01); *A61M 2205/584* (2013.01)

(58) Field of Classification Search
CPC ........... A61M 25/0015; A61M 25/0029; A61M 25/007; A61M 25/0097; A61M 25/0014; A61M 39/10
See application file for complete search history.

(56) References Cited

U.S. PATENT DOCUMENTS

| | | | | |
|---|---|---|---|---|
| 4,846,005 | A | * 7/1989 | Bacehowski | A61J 1/10 73/864.81 |
| 5,141,850 | A | * 8/1992 | Cole | G01N 33/558 422/417 |

(Continued)

*Primary Examiner* — Adam Marcetich
*Assistant Examiner* — Ted Yang
(74) *Attorney, Agent, or Firm* — The Watson IP Group, PLC; Jovan N. Jovanovic

(57) ABSTRACT

An extension assembly for a catheter comprises an extension tube, an extension connector, and an indicator assembly. The extension tube has a proximal end and a distal end. The extension tube further has an inner bore and an opening placing an interior of the extension tube in fluid communication with an exterior of the extension tube. The extension connector is coupled to the proximal end of the extension tube. The indicator assembly is comprised of a sealing member, a wicking member, and an indicator. The sealing member including a first side and a second side. The wicking member includes a wicking tab to be disposed within the opening of the extension tube. The indicator is in fluid communication with the wicking member. The sealing member is at least partially clear to allow visual inspection of the indicator once the indicator assembly is coupled to the extension tube.

14 Claims, 14 Drawing Sheets

Related U.S. Application Data continuation-in-part of application No. 17/108,838, filed on Dec. 1, 2020, now Pat. No. 11,752,298.

(60) Provisional application No. 63/042,770, filed on Jun. 23, 2020, provisional application No. 62/948,304, filed on Dec. 15, 2019.

(56) References Cited

U.S. PATENT DOCUMENTS

| | | | | |
|---|---|---|---|---|
| 5,312,379 | A * | 5/1994 | Rahe | A61B 5/20 600/584 |
| 6,375,627 | B1 * | 4/2002 | Mauze | A61B 5/15107 600/584 |
| 6,375,897 | B1 * | 4/2002 | Bachand | A61B 10/007 604/404 |
| 2007/0092402 | A1 * | 4/2007 | Wu | B01L 3/502 422/400 |
| 2007/0148716 | A1 * | 6/2007 | Gorres | G01N 33/569 435/287.2 |
| 2009/0137887 | A1 * | 5/2009 | Shariati | A61B 5/14542 600/345 |
| 2018/0356413 | A1 * | 12/2018 | Parekh | A61M 1/287 |
| 2019/0240063 | A1 * | 8/2019 | Doreswamy | A61F 5/4553 |
| 2019/0277835 | A1 * | 9/2019 | Suarez del Real Pena | G01N 33/84 |
| 2021/0178117 | A1 * | 6/2021 | McDonnough | A61M 39/10 |
| 2021/0308419 | A1 * | 10/2021 | McDunnough | A61M 25/0023 |

* cited by examiner

SELF-INTERMITTENT URINARY CATHETER EXTENSION WITH INFECTION DETECTION, A CATHETER ASSEMBLY HAVING AN EXTENSION WITH INFECTION DETECTION AND A CATHETER ASSEMBLY HAVING INFECTION DETECTION

CROSS-REFERENCE TO RELATED APPLICATION

This present application is a continuation of U.S. patent application Ser. No. 17/337,350 filed Jun. 2, 2021, entitled "SELF-INTERMITTENT URINARY CATHETER EXTENSION WITH INFECTION DETECTION, A CATHETER ASSEMBLY HAVING AN EXTENSION WITH INFECTION DETECTION AND A CATHETER ASSEMBLY HAVING INFECTION DETECTION", which is a continuation-in-part of U.S. patent application Ser. No. 17/108,838 filed Dec. 1, 2020, entitled "SELF-INTERMITTENT URINARY CATHETER EXTENSION WITH INFECTION DETECTION, A CATHETER ASSEMBLY HAVING AN EXTENSION WITH INFECTION DETECTION AND A CATHETER ASSEMBLY HAVING INFECTION DETECTION", which claims priority from U.S. Provisional Patent Application Ser. No. 62/948,304, filed Dec. 15, 2019, entitled "Self-Intermittent Urinary Catheter Extension With Infection Detection And A Catheter Assembly Having An Extension With Infection Detection", and also U.S. Provisional Patent Application Ser. No. 63/042,770 filed Jun. 23, 2020, entitled "Self-Intermittent Urinary Catheter Extension With Infection Detection And A Catheter Assembly Having An Extension With Infection Detection", the entire disclosure of each of these applications is hereby incorporated by reference in their respective entirety.

This application is also related to, but does not claim priority from, U.S. patent application Ser. No. 16/405,961 filed May 7, 2019, entitled "Monolithic Self-Intermittent Catherization System with Attached Extension". The disclosure of this application is hereby incorporated by reference in its entirety.

BACKGROUND OF THE DISCLOSURE

1. Field of the Disclosure

The disclosure relates in general to self-intermittent urinary catheters, and more particularly, to a self-intermittent urinary catheter extension with infection detection. It will be understood that the system of the present disclosure is not limited to self-intermittent catheters, but can be utilized in association with, among other structures, indwelling catheter systems, without limitation.

2. Background Art

The urinary tract consists of the kidneys, bladder, ureters, and urethra. Urine in the bladder is normally sterile. This means it does not contain any bacteria or other germs (such as fungi). But bacteria can enter the urinary tract through the urethra. This can cause a urinary tract infection (UTI). A UTI can happen anywhere in your urinary tract, including your bladder, ureters, kidneys, and urethra. Most UTIs are easy to cure with antibiotics. But an untreated infection can become more severe as it spreads toward the kidneys. An infection in the upper urinary tract is much more challenging to treat. Eventually, the infection can spread into your blood, causing sepsis and frequently, death.

Individuals with spinal cord injuries or other maladies that preclude them from sensation in their lower body have Neurogenic bladders, which necessitates them to void their bladder 5 to 7 times a day through use of a self-intermittent urinary catheter. Because of limited sensation, UTIs are not sensed right away and therefore, treatment is late. There is an extremely high incidence of UTIs and subsequent complications in this population due to these issues, frequently resulting in complications, other medical issues, hospital stays, and often—sepsis and death.

SUMMARY OF THE DISCLOSURE

The disclosure is directed to an extension assembly for a catheter comprising an extension tube, an extension connector, and an indicator assembly. The extension tube has a proximal end and a distal end. The extension tube further has an inner bore and an opening placing an interior of the extension tube in fluid communication with an exterior of the extension tube. The extension connector is coupled to the proximal end of the extension tube. The indicator assembly is comprised of a sealing member, a wicking member, and an indicator. The sealing member including a first side and a second side. The wicking member includes a first side, a second side, and a wicking tab, the first side of the wicking member being disposed against the second side of the sealing member and the wicking tab to be disposed within the opening of the extension tube. The indicator includes a first side and a second side, the first side of the indicator being disposed against the second side of the wicking member such that the indicator is in fluid communication with the wicking member. The sealing member is at least partially clear to allow visual inspection of the indicator once the indicator assembly is coupled to the extension tube.

In some configurations, the indicator is a first indicator, the extension assembly further comprising a second indicator including a first side and a second side, the first side of the second indicator being disposed against the second side of the wicking member such that the second indicator is in fluid communication with the wicking member.

In some configurations, the first indicator tests for Nitrite and the second indicator tests for Leukocyte.

In some configurations, the opening is a slotted passage.

In some configurations, a length of the slotted passage extends along a length of the extension tube.

In some configurations, the wicking tab is rectangular in shape.

In some such configurations, approximately half of a height of first side of the indicator is disposed against the second side of the wicking member, and approximately half of the height of the first side of the indicator is disposed on the second side of the sealing member.

In some configurations, the wicking member is approximately 0.20" in height and 1.00" in length.

In some configurations, the indicator is approximately 0.20" in height and 0.90" in width.

In some configurations, the indicator wraps substantially around the extension tube.

In some configurations, a bag coupling connector is coupled to the distal end of the extension tube.

In some configurations, the sealing member is square in shape.

In some configurations, the sealing member is one of a plastic tape and a shrink wrap.

In some configurations, the indicator is approximately square in shape.

In another aspect of the disclosure, the disclosure is directed to a catheter comprising a catheter tube, an extension tube, an extension connector, and an indicator assembly. The catheter tube has a proximal end and a distal end, the catheter having an inner bore. The extension tube having a body with a central bore, with the proximal end of the catheter tube coupled to the first end of the body, the extension tube further comprising a proximal end and a distal end, the extension tube having an inner bore and an opening placing an interior of the extension tube in fluid communication with an exterior of the extension tube. The extension connector is coupled to the proximal end of the extension tube. The In some configurations, the at least one slot further comprises a substantially rectangular lower end wall, and wherein the upstanding walls further comprise a catheter side wall, an extension side wall spaced apart from the extension side wall, with a first joining wall spanning therebetween and a second joining wall spanning therebetween spaced apart from the first joining wall. The indicator assembly is comprised of a sealing member, a wicking member, and an indicator. The sealing member including a first side and a second side. The wicking member includes a first side, a second side, and a wicking tab, the first side of the wicking member being disposed against the second side of the sealing member and the wicking tab to be disposed within the opening of the extension tube. The indicator includes a first side and a second side, the first side of the indicator being disposed against the second side of the wicking member such that the indicator is in fluid communication with the wicking member. The sealing member is at least partially clear to allow visual inspection of the indicator once the indicator assembly is coupled to the extension tube.

In some configurations of the catheter, the indicator is a first indicator, the extension assembly further comprising a second indicator including a first side and a second side, the first side of the second indicator being disposed against the second side of the wicking member such that the second indicator is in fluid communication with the wicking member.

In some configurations of the catheter, approximately half of a height of first side of the indicator is disposed against the second side of the wicking member, and approximately half of the height of the first side of the indicator is disposed on the second side of the sealing member.

In some configurations of the catheter, the indicator wraps substantially around the extension tube.

In some configurations of the catheter, the sealing member is one of a plastic tape and a shrink wrap.

BRIEF DESCRIPTION OF THE DRAWINGS

The disclosure will now be described with reference to the drawings wherein.

DETAILED DESCRIPTION OF THE DISCLOSURE

Figure 1:
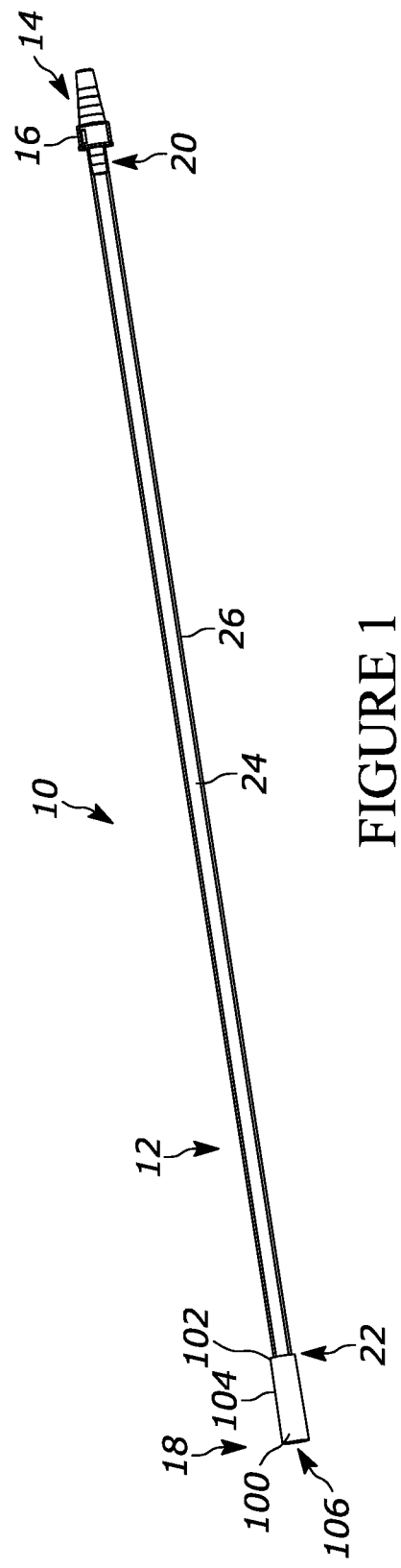
FIG. 1 of the drawings is a side elevational view of an extension assembly of the present disclosure, showing, the extension tube, the extension connector, the indicator assembly and the bag coupling connector.

While this disclosure is susceptible of embodiment in many different forms, there is shown in the drawings and described herein in detail a specific embodiment(s) with the understanding that the present disclosure is to be considered as an exemplification and is not intended to be limited to the embodiment(s) illustrated.

It will be understood that like or analogous elements and/or components, referred to herein, may be identified throughout the drawings by like reference characters. In addition, it will be understood that the drawings are merely schematic representations of the invention, and some of the components may have been distorted from actual scale for purposes of pictorial clarity.

Figure 2:
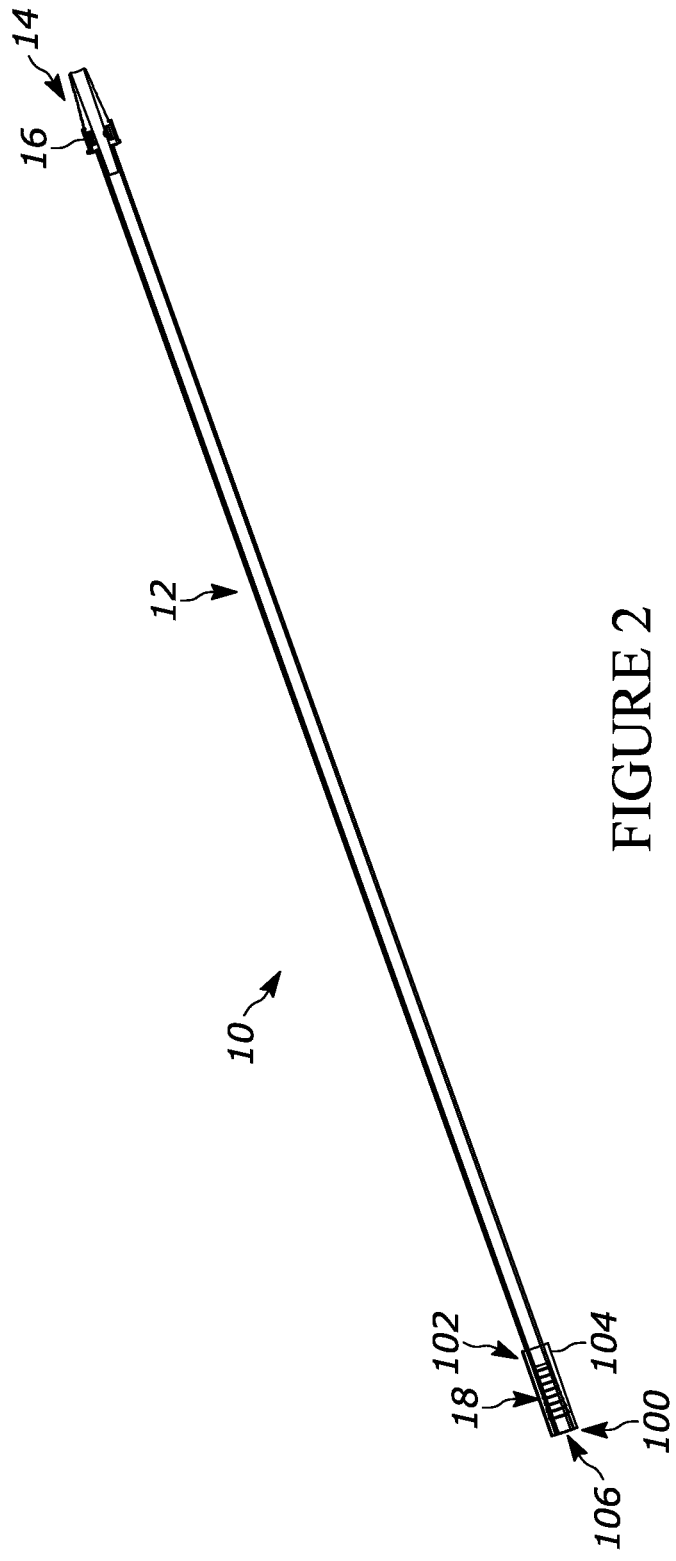
FIG. 2 of the drawings is a cross-sectional view of the extension assembly of FIG. 1, taken about the longitudinal axis of the same.

Referring now to the drawings and in particular to FIGS. 1 and 2, the self-intermittent urinary catheter extension assembly (herein referred to as "extension assembly") is shown generally at 10. As will be explained below, the extension assembly is configured for coupling to a self-intermittent urinary catheter. The extension assembly is not limited to use therewith, but can also be used with other types of catheters, and can also be used in closed systems, such as, for example indwelling catheters and Foley catheters, among others. For illustrative purposes only, and not for limiting purposes, the extension assembly will be described in the environment of a self-intermittent urinary catheter with the understanding that it is not so limited in use.

The extension assembly 10 is shown as comprising extension tube 12, extension connector 14, indicator assembly 16 and bag coupling connector 18. The extension tube 12 is shown as comprising a tubular member formed from a polymer, such as a latex free polymer. In many configurations, the tubular member may be clear and transparent, while in other configurations, the tubular member may be translucent or opaque and in varying colors. The extension tube 12 extends between proximal end 20 and distal end 22. The extension tube defines an outer surface 26 and an inner bore 24, which, in the configuration shown, defines a substantially uniform cylindrical configuration with a substantially uniform wall thickness. Of course, variations are contemplated in the configuration and cross-sectional shape of the extension tube.

The extension connector 14 comprises body 30 and cover member 78. The body 30 preferably comprises an injection molded rigid polymer component that is integrally formed and monolithic. Of course, multiple component constructions are likewise contemplated, wherein the multiple components can be co-molded, or separately molded and attached together mechanically through mechanical coupling, adhesive coupling and/or welding or the like. The body 30 extends from first end 32 to second end 34 and central bore 36. In the configuration shown, the central bore is substantially circular in cross-sectional configuration while variations are contemplated.

The body 30 further defines a tube coupling assembly 40, a catheter coupling assembly 50 and a central test portion 56. In the configuration shown, the tube coupling assembly is configured to be attachable to the extension tube. The tube coupling assembly includes outer surface 42 and proximal stop 44. In one configuration, the proximal stop defines a flange, such as flange 46 which provides a positive stop as the extension tube is extended over the outer surface of the tube coupling assembly. The outer surface 42, in the configuration shown defines a plurality of barbs which are configured to sealingly engage the inner bore 24 of the extension tube in engagement. It will be understood that the relative sizes are such that the extension tube is both sealed against the outer surface of the tube coupling assembly and that it is also resistant to separation. In such a configuration, the extension tube is stretched over the barbs of the outer surface.

Figure 8:
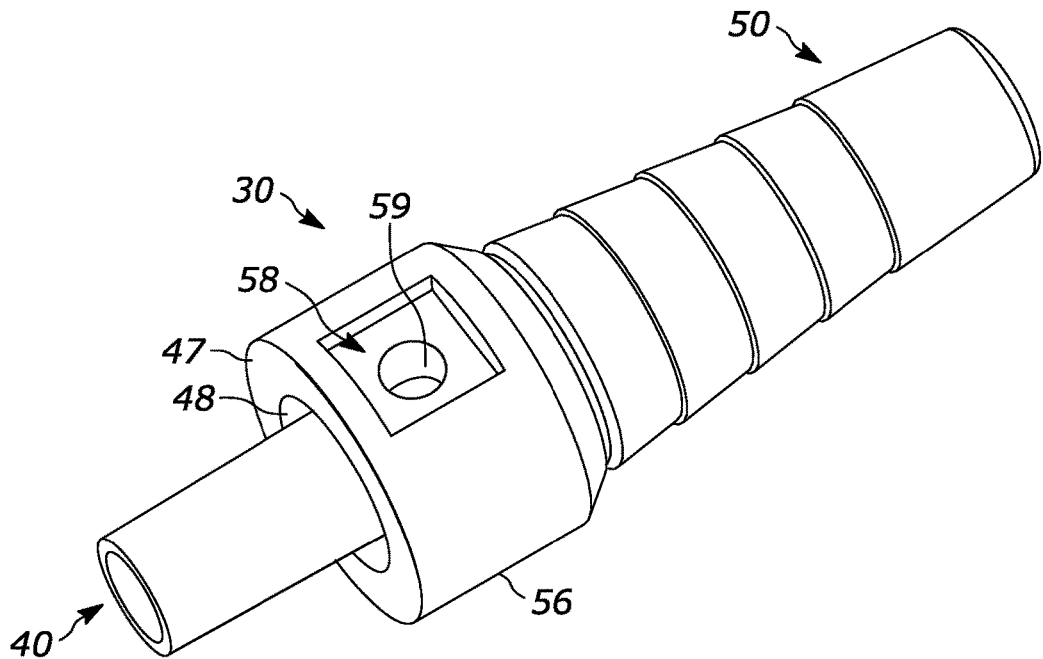
FIG. 8 of the drawings is a perspective view of an extension connector, showing, in particular, a configuration of the tube coupling assembly having an outer rim and a cavity.
Figure 9:
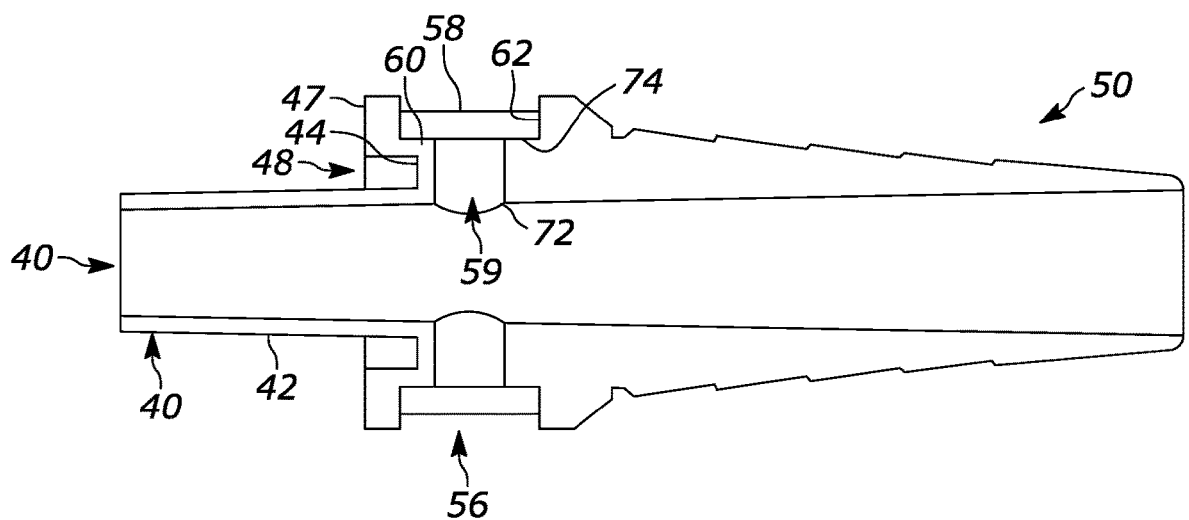
FIG. 9 of the drawings is a cross-sectional view of the extension connector of FIG. 8.

In another configuration, the outer surface may be substantially smooth and the extension tube may be slid over through stretching (wherein reliance is made on the inward biasing of the extension tube) or through an adhesive. In some configurations, such as the configuration shown in FIGS. 8 and 9, a cavity 48 may be created at the inner end of the tube coupling assembly which can be defined by an outer rim 47 that is concentric with and spaced apart from the outer surface 42 of the tube coupling assembly 40. It will be understood that various combinations of outer surfaces and various couplings (mechanical through stretching, adhesive or the like) can be combined with each other to create variations on the different structures disclosed herein.

Figure 3:
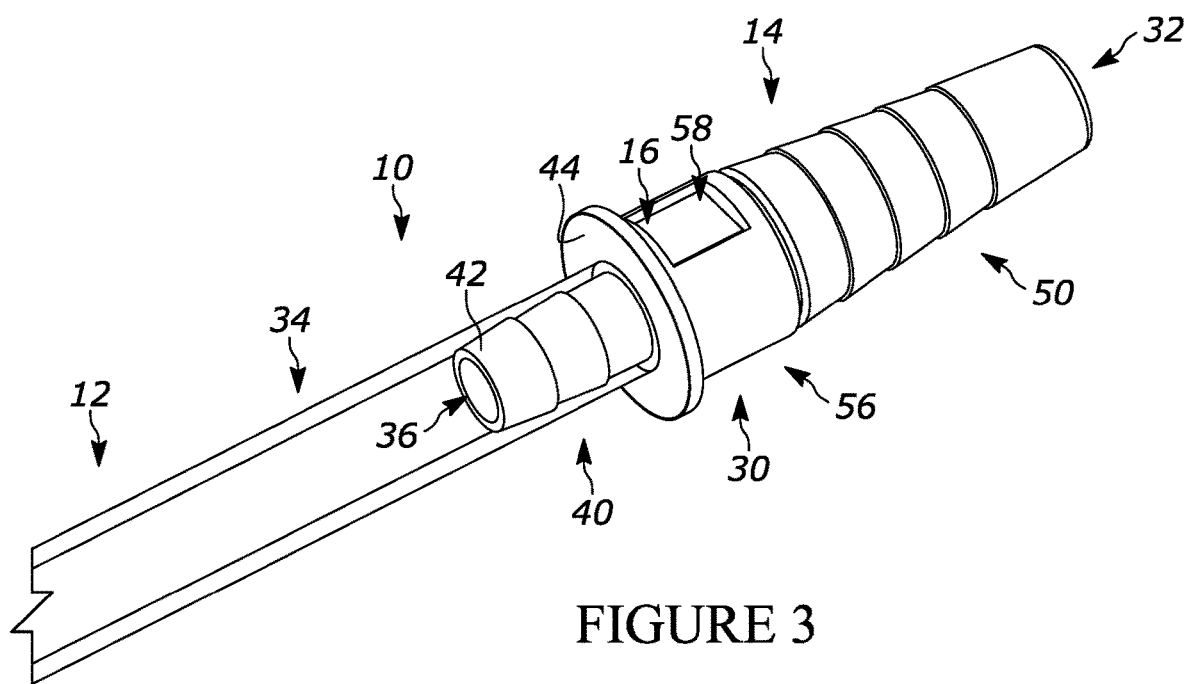
FIG. 3 of the drawings is a partial perspective view of the extension assembly, showing, in particular, the extension connector and indicator assembly of the present disclosure.
Figure 3A:
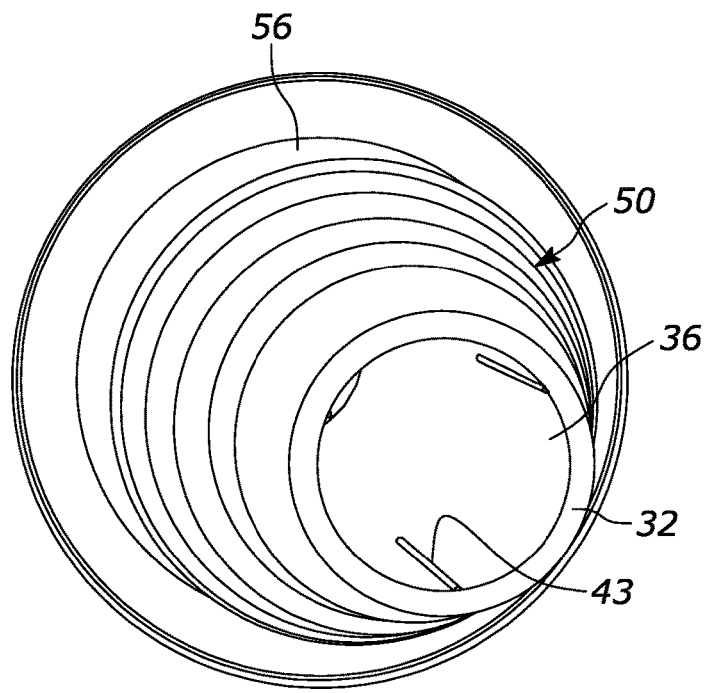
FIG. 3A of the drawings is a perspective view of the extension connector, showing, in particular ribs that extend radially inwardly within the central bore.
Figure 4:
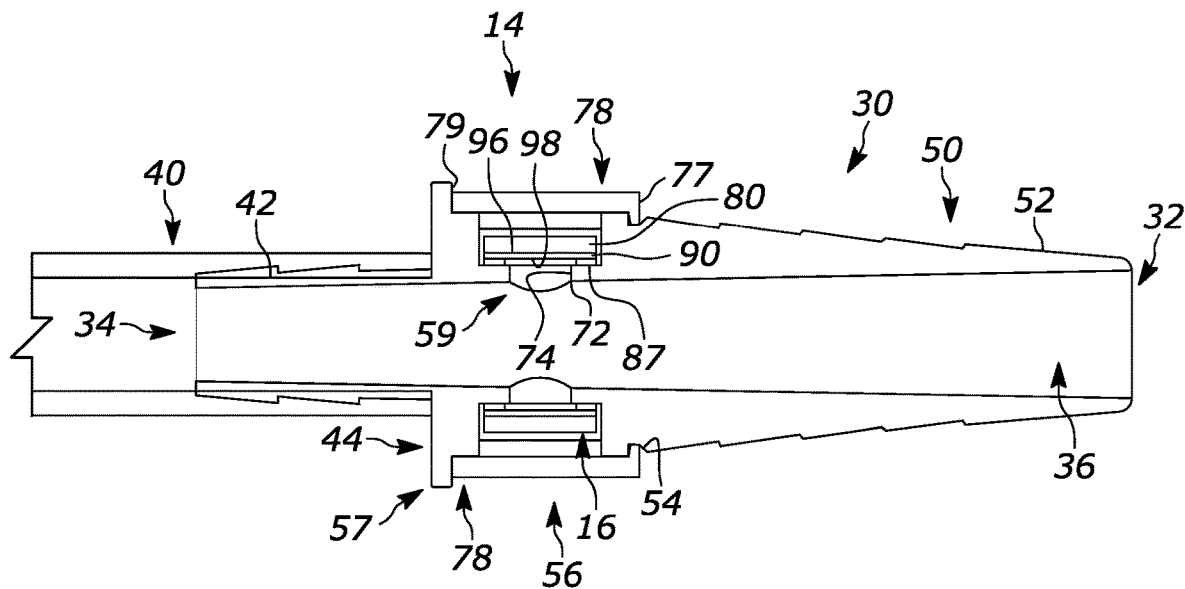
FIG. 4 of the drawings is a partial cross-sectional view of the extension assembly, showing, in particular, the central test portion having a plurality of slots therein, with a plurality of radial passages (one for each of the slots), with the indicator assembly having an indicator, a wicking member and a liner.
Figure 5:
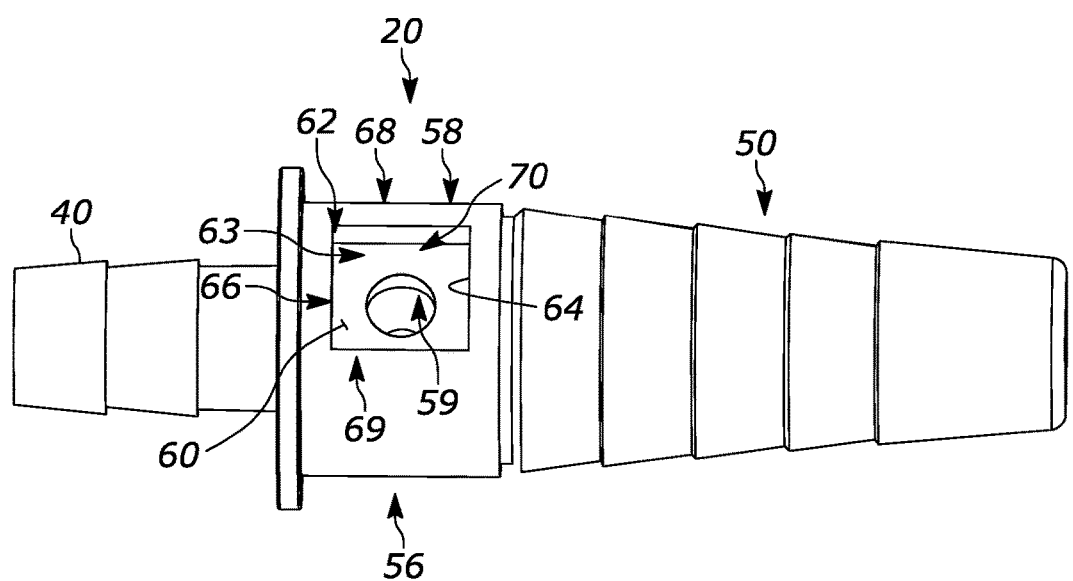
FIG. 5 of the drawings is a side elevational view of the extension connector of the present disclosure, showing, in particular, details pertaining to the slot and the radial passage of a configuration.
Figure 6:
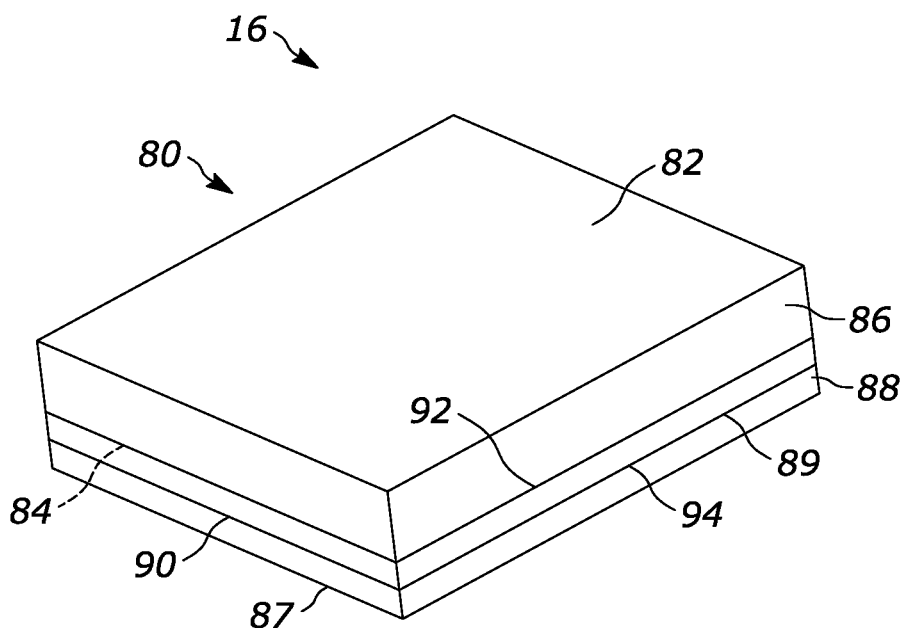
FIG. 6 of the drawings is an upper perspective view of a configuration of the indicator assembly.
Figure 7:
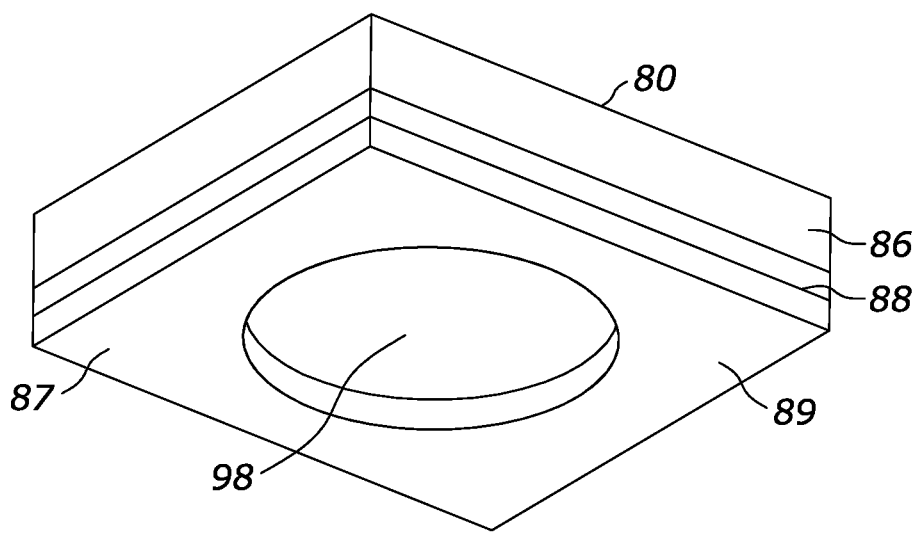
FIG. 7 of the drawings is a lower perspective view of a configuration of the indicator assembly of FIG. 6.

The catheter coupling assembly 50 is shown in FIG. 3 through 5 as comprising outer surface 52 and proximal stop 54. In the configuration shown, the proximal stop comprises a ridge 55 representing the proximal end of the catheter coupling assembly. The outer surface 52 comprises a barbed configuration of slightly increasing diameter. Such a configuration allows for the sealed engagement with a variety of catheters in a sealed arrangement. In other configurations, a fewer or greater amount of barbs as well as greater dimensional changes are contemplated. Furthermore, it is contemplated that in still other configurations, the outer surface may comprise a smooth surface, or a different configured surface for engagement in a sealed manner with the catheter (or another tubular member). With reference to FIG. 3A, the central bore 36 thereof may include inwardly directed ribs 43 that extend along the central bore generally along the length thereof at least partially between a first and second end thereof. These ribs 43 increase the turbulence of the fluid within the central bore and provide improved contact between the fluid (urine) and the radial passage (so that the fluid can improve contact with the indicator assembly). In the configuration shown, a plurality of ribs 43 (in the configuration shown, three ribs spaced at 120° from each other) extend longitudinally along the central bore between the radial passage and the first end of the extension connector.

As to the central test portion, a plurality of central test portions 56 may be positioned radially separated from each other about the central portion 57 of the body 30. In the configuration shown, two central test portions are positioned 180° apart from each other, or, on opposite sides of each other. In other configurations, a single central test portion may be utilized. In still other configurations, more than two central test portions may be disposed along the central portion of the body. It will be understood that in the configuration shown, the pair of central test portions are substantially identical to each other, while, in other configurations, the different test portions may have different configurations (which may be due to positioning, due to different testing structures positioned therein, among other variations). As such, one of the central test portions will be described with the understanding that the other test portion may be substantially the same in configuration.

The central test portion 56, in the configuration depicted, comprises slot 58 and radial passage 59. The slot 58 is defined by lower end wall 60 and upstand walls 62 which collectively define cavity 63 and upper opening 70. In the configuration shown, the slot comprises a substantially rectangular slot having a substantially planar and rectangular lower end wall 60, a catheter side wall 64, an extension side wall 66, a first joining wall 68 and a second joining wall 69. The joining walls are generally perpendicular to the lower end wall 60. The width and length of the resulting slot are dimensionally larger than the height thereof.

While a rectangular configuration is shown, the slot is not limited to such a configuration. For example, the slot may comprise a cylindrical configuration, with the lower end wall being substantially circular. Other polygonal configurations are contemplated, such as triangular or hexagonal lower end walls. Furthermore, it is contemplated that the base surface may be arcuate so as to be concentric with the inner bore 24 of the extension connector 14. Additionally, it is contemplated that the upstanding joining walls may comprise walls that are perpendicular to the arcuate lower end wall, or, where the lower end wall is planar, the upstanding joining walls may be oblique thereto. Furthermore, it is contemplated that each wall may be disposed at a different angle relative to the lower end wall. It is likewise contemplated that the upstanding walls may be other than substantially planar.

Figure 10:
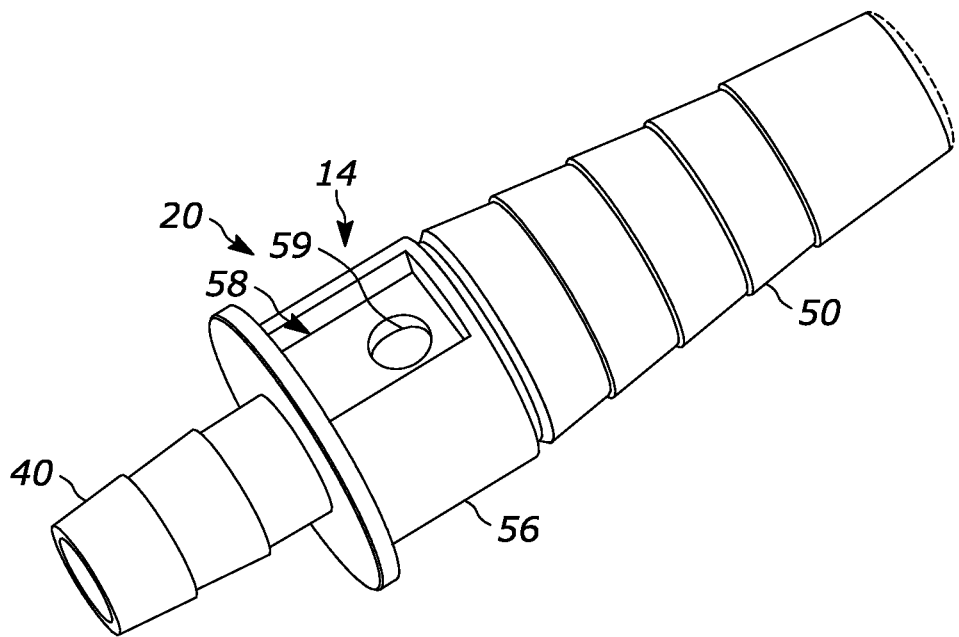
FIG. 10 of the drawings is a perspective view of an extension connector, showing, in particular, a configuration of the central test portion having a radial passage that is offset toward the catheter side wall, and, in the configuration shown, positioned between the first and second joining walls.
Figure 11:
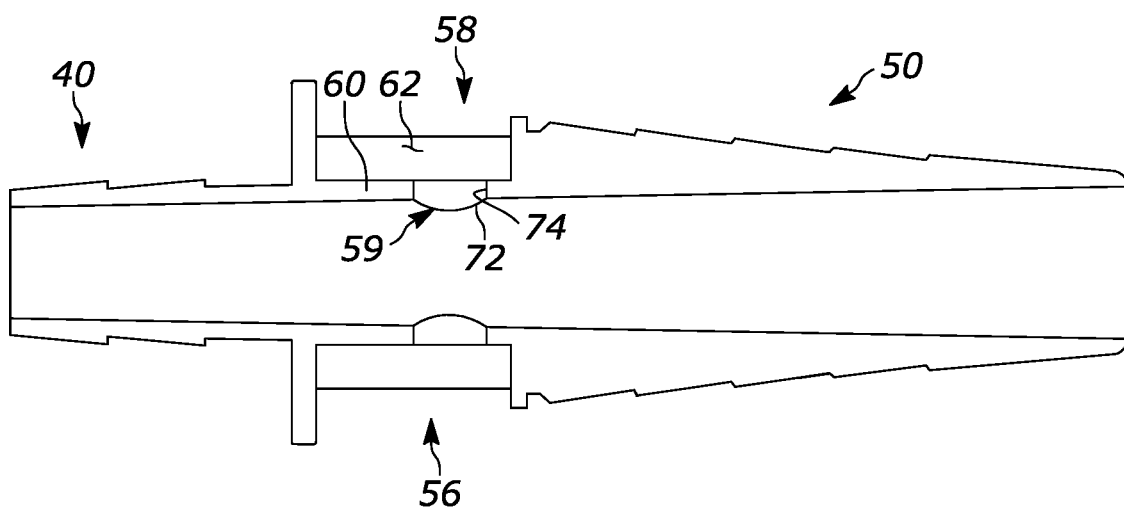
FIG. 11 of the drawings is a cross-sectional view of the extension connector of FIG. 10.

The radial passage 59 is shown in FIGS. 4 and 5 as comprising a passage that includes inner end 72 and outer end 74. The radial passage places the cavity 63 in fluid communication with the central bore 36 of the extension connector. In the configuration shown, the radial passage may comprise a bore that extends through the lower end wall. Such an opening is dimensionally smaller than either the width or the length of the lower end wall. Such an opening may be centrally located, or may be offset to any one of the walls (typically, toward one of the catheter side wall 65 or the extension side wall 66, FIGS. 10 and 11). In the configuration shown, the bore comprises a cylindrical configuration, while other configurations are contemplated.

Figure 12:
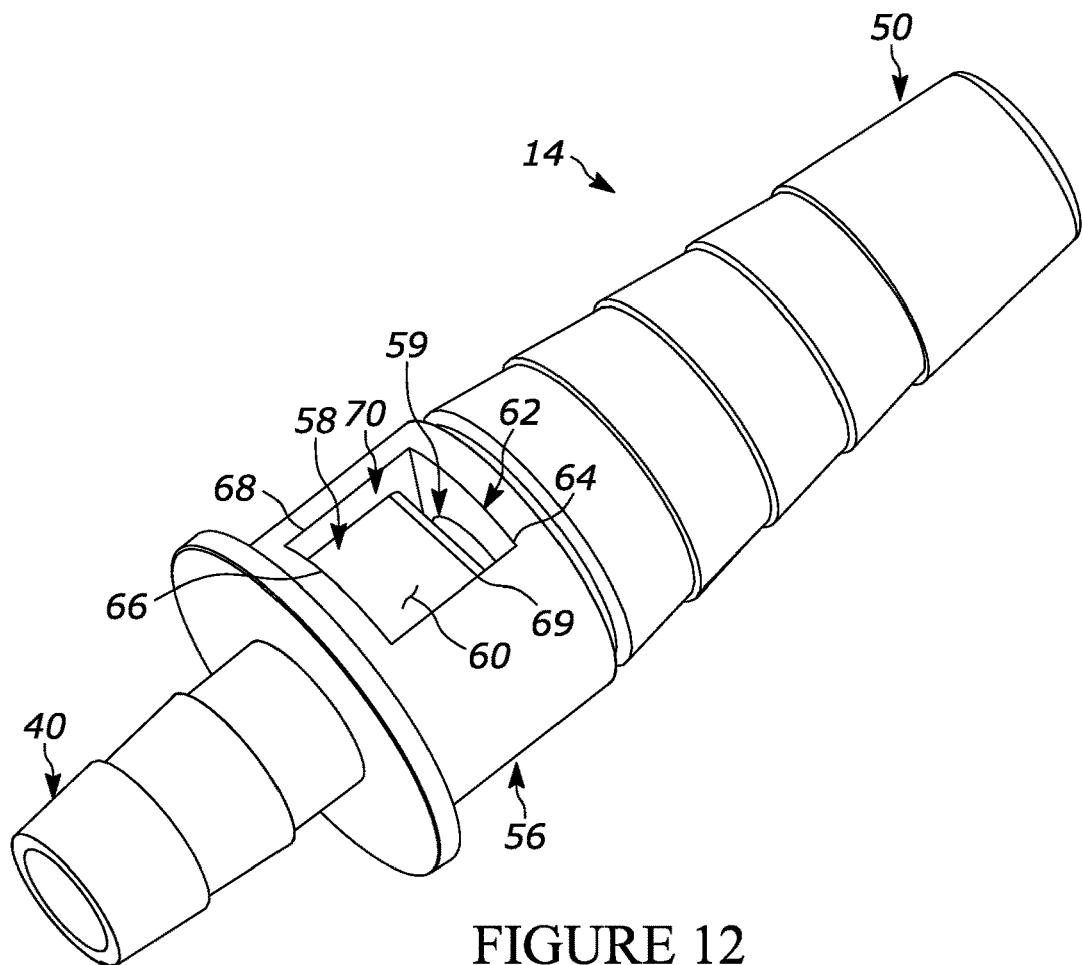
FIG. 12 of the drawings is a perspective view of an extension connector, showing, in particular, a configuration of the central test portion having a slot passage that is positioned along the catheter side wall and which extends between the first and second joining walls.
Figure 13:
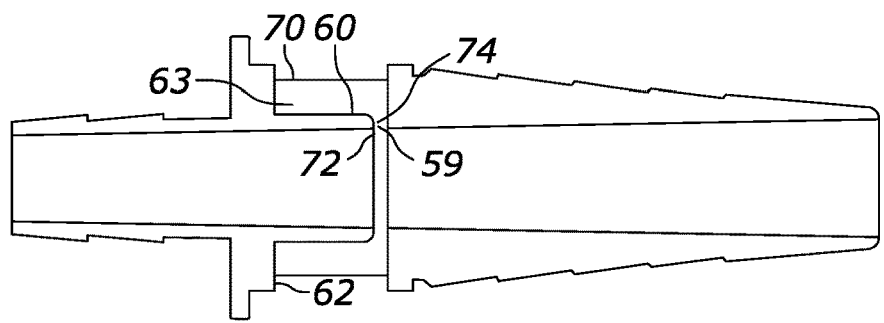
FIG. 13 of the drawings is a cross-sectional view of the extension connector of FIG. 12.
Figure 14:
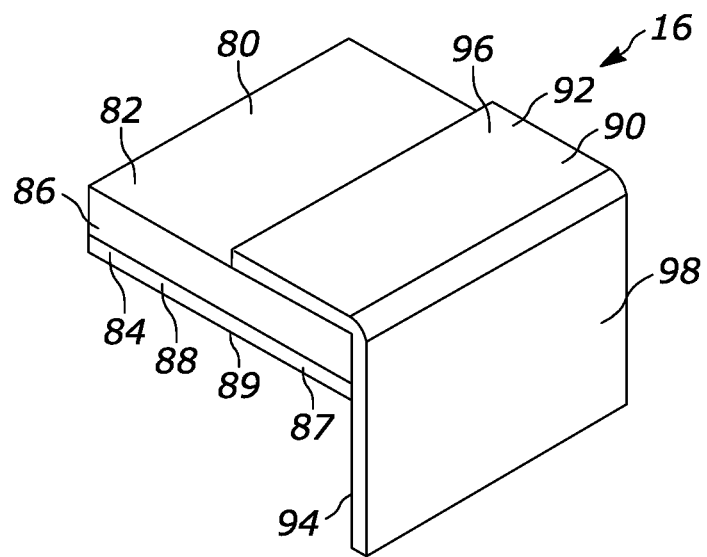
FIG. 14 of the drawings is a perspective view of a configuration of the indicator assembly of the present disclosure, which may be utilized with the extension connector shown in FIGS. 12 and 13.
Figure 15:
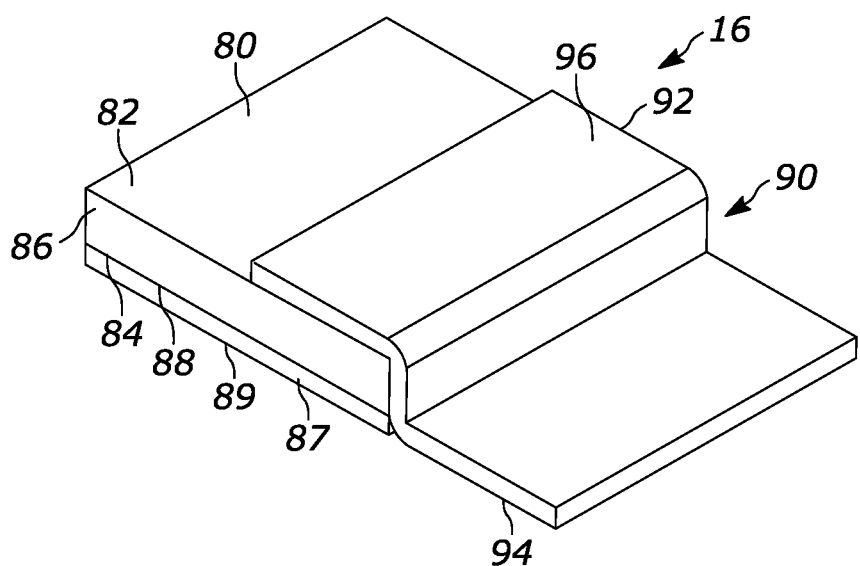
FIG. 15 of the drawings is a perspective view of a configuration of the indicator assembly of the present disclosure, which may be utilized with the extension connector shown in FIGS. 10 and 11.

In another configuration, as is shown in FIGS. 12 and 13, the radial passage may comprise a slot, that for example, extends between the first joining wall and the second joining wall proximate the catheter side wall, for example. In other configurations, the slot may be spaced apart from the catheter side wall or the extension side wall or adjacent either one (or both). In other configurations, such a slot may be positioned in alternate directions, such as for example, between the catheter side wall and the extension side wall, and along one of the first and second joining walls.

A cover member 78 (FIG. 4) may span across a portion of the central test portion 56 that is on opposing sides of the slot 58 so as to provide a substantially (if not fully) fluid tight cover over the upper opening 70 of the central test portion. It is contemplated that at least a portion of the cover member will include a transparent portion so as to provide visual access to the slot for purposes of observing the indicator assembly. In the configuration shown, the cover member comprises a hoop-like structure having a catheter side seal 77 and an extension side seal 79 that seals against opposing surfaces that matingly engage with the same. In other configurations, the cover member may be coupled to the central test portion through an adhesive in place or in addition to a mechanical coupling.

With additional reference to FIGS. 6, 7, 14 and 15, the indicator assembly 16 includes an indicator 80, a wicking member 90 and a liner 87. In the configurations shown, the indicator includes a top surface 82, a bottom surface 84 opposite the top surface 82 and edges 86 which define the shape of the indicator assembly. As will be understood, the indicator comprises a woven or non-woven material (such as an absorbent pad or the like) which includes a chemical that has a color reaction to a particular substance. That is, the presence of the substance triggers a color change providing a visual confirmation of the presence of the substance. The particular substance that is monitored can be varied, with the understanding that, for purposes of the present disclosure, the substance to be monitored provides an indication of a bladder infection. In the configuration contemplated, the indicator comprises a material that is available from Teco Diagnostics of Anaheim, California. Other materials are contemplated for use therewith.

The wicking member includes an upper surface 92, a lower surface 94, an indicator contact portion 96 and a flow contact portion 98. The upper and lower surfaces generally are planar and define a wicking member, in the present configuration, that is substantially uniform in thickness, and substantially flexible. An edge defines the outer perimeter of the wicking member. The wicking member essentially provides for the delivery of fluid at a controlled rate or a controlled flow or volume from the flow of urine to the indicator 80. In various configurations, a portion of the wicking member is in fluid communication with the flow of urine through the central bore, and that portion comprises the flow contact portion 98. Additionally, a portion of the wicking member is in fluid communication with a surface and/or an edge of the indicator thereby defining the indicator contact portion 96. In the configurations shown, the wicking material is in physical contact with the indicator. In the configuration shown, the wicking member comprises a material likewise available from Teco Diagnostics of Anaheim, California.

In some configurations, the wicking member remains within the slot, entirely. In other configurations, the wicking member is positionable within the slot, with a portion of the wicking member extending into the radial passage (FIGS. 12, 13, and the indicator assembly of FIG. 14). For example, the wicking member may extend into the radial passage where, again, for example, and not to be deemed limiting, the radial passage comprises a slot extending from the first joining wall to the second joining wall along one or both of the catheter side wall and/or the extension side wall. It will be understood that, in other configurations as well, the wicking member may extend into the radial passage, and may be shaped so as to extend into the radial passage in a particular configuration and/or orientation.

The liner 87 includes an upper surface 88 and a lower surface 89 the upper and lower surfaces cooperate to define an outer perimeter. The liner is preferably utilized to preclude and/or limit the exposure and/or movement of fluid either to or from the indicator. In some configurations, the liner overlies a portion of or an entirety of a surface (such as the bottom surface) of the indicator when the indicator is positioned within the slot. In at least some configurations, the liner is sandwiched between the bottom surface of the indicator and the lower end wall 60 of the slot 58. In some configurations, the liner may be continuous or may include openings. In one such configuration of FIGS. 1 through 5, the liner is sandwiched between the lower surface of the wicking member and the lower end wall of the slot of the central test portion. In such a configuration, the liner includes an opening so as to allow direct contact of fluid from within the central bore to communicate with the wicking member.

In the configurations shown, the indicator generally has a square configuration that matches the shape of the slot 58. In other configurations, it will be understood that the shape of the slot may be varied, and according, the shape of the indicator. In other configurations, it will be understood that the shapes may not match, or may match. It will further be understood that in some configurations, the edges of each of the indicator, the wicking member and the liner may be identical, whereas in other configurations, the wicking member may extend along various surfaces and may extend as an appendage from the indicator and/or the liner. Various combinations of the same are contemplated.

It is also contemplated that the indicator assembly may extend fully around the entirety of the extension connector, and, may be positioned in the central test portion, or may be positioned elsewhere. For example, in some configurations, a slot may be provided in the tube coupling assembly as opposed to the central test portion, and an edge thereof may be exposed to the stream.

The bag coupling connector is shown in FIGS. 1 and 2 as comprising outer end 100, inner end 102, outer surface face 104 and central bore 106. The bag coupling connector can be extended over the distal end of the extension and may be coupled to a bag. In other configurations, the extension may be directed to a toilet, a urinal, or to a collection container and may be loosely associated with the same, in place of being coupled thereto by way of the bag coupling connector or the like.

In operation, as the catheter is utilized, there is flow of urine through the inner bore of the extension assembly, and then the central bore of the extension connector. The flow of urine through the central bore of the extension connector eventually directs at least some portion of urine through one of the radial passages 59 in the central test portion. As the urine passes through the radial passage, the urine contacts the wicking member 90. The wicking member 90 through wicking action pulls the urine into the wicking member and directs the urine from the flow contact portion toward and into the indicator contact portion of the wicking member. Continued wicking eventually has urine reach the indicator. As the urine interacts with the indicator, if certain chemicals are present, then the indicator will experience a color change indicative of the presence of the chemical. The presence of the chemical is an indication that there is a high probability of a bladder infection. On the other hand, if there is no color change, there is indication that the bladder is free of infection.

By transferring the urine from the flow to the indicator through the wicking member, the amount of urine that reaches the indicator can be minimized. Such minimization precludes the inadvertent removal of the underlying test chemicals within the indicator and generally preclude the bleeding out of the chemical from the indicator. Additionally, the liner 87 further precludes the bleeding out of the chemical from the indicator, leaving sufficient chemicals to allow for the indicator to effectively point out, or, identify, the presence or absence of an infection.

Figure 16:
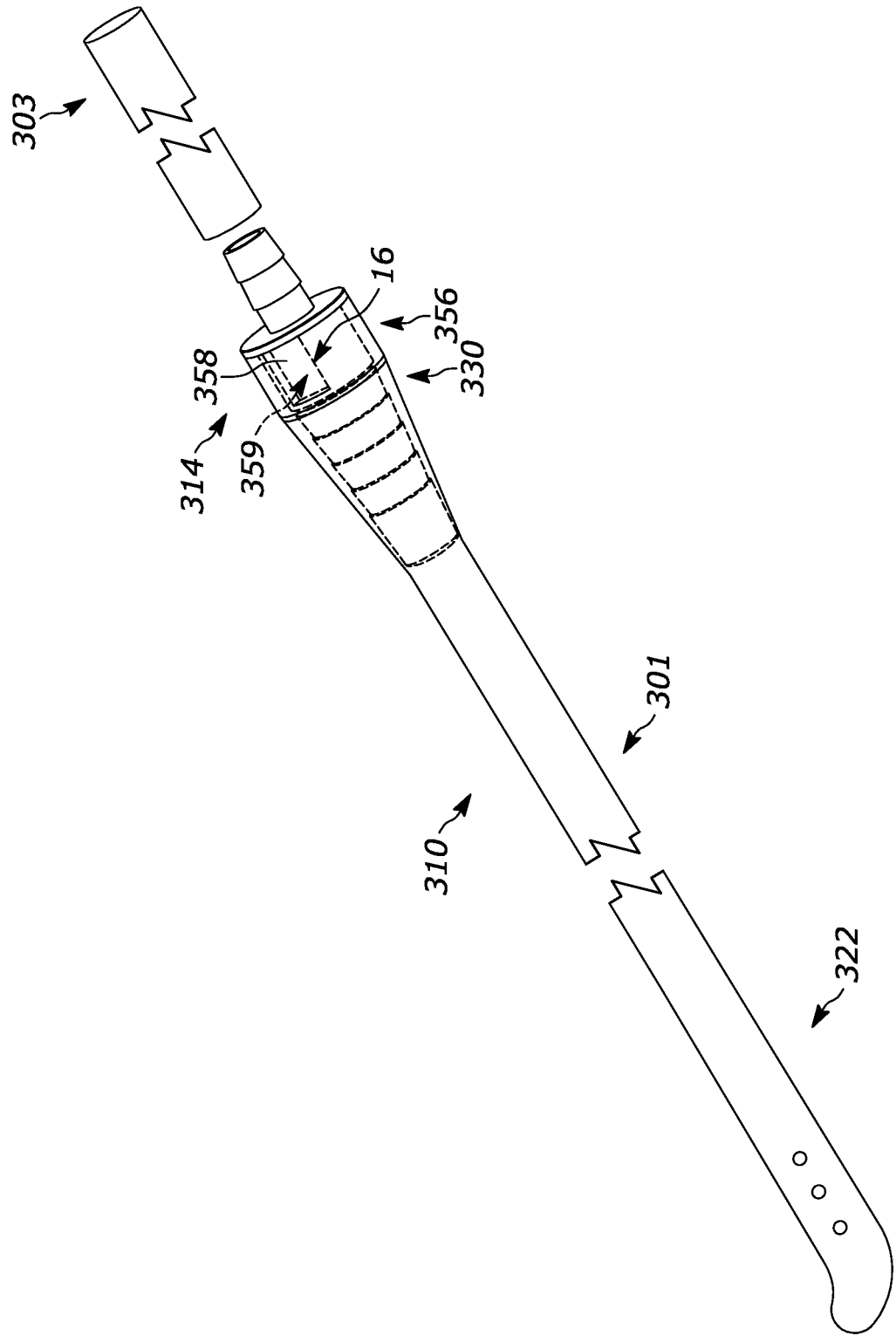
FIG. 16 of the drawings is a perspective view of a catheter having the central test portion of the present disclosure.

It will be understood that the same principles that are in the extension connector can be applied to a catheter itself. That is, the body of the catheter can have the structural features of the central test portion of the body and the indicator assembly. One such configuration is shown in FIG. 16. In such a configuration, the catheter assembly 310 includes catheter tube 301, and connector 314. The central test portion 356, and in particular the slot 358 and the radial passage 359 thereof (in addition to the cover) can be adapted to the body of the catheter. The structure of the central test portion 356 may be similar to, or identical to the central test portion of the extension connector (FIGS. 1 through 14), as can the indicator assembly 16.

As with the extension tube, the catheter tube 312 is similar to an extension tube, having a distal end 322 that allows for insertion into the body. As will be understood, the distal end is shaped so as to extend into the body, and includes openings that are placed in fluid communication with the urine in the bladder of a user.

The catheter tube 312 can be coupled to the body 330 in place of the catheter coupling assembly of the extension connector. The opposing end can be coupled to an extension 303 or the like, directly, or through other structures known to one of skill in the art.

Figure 17:
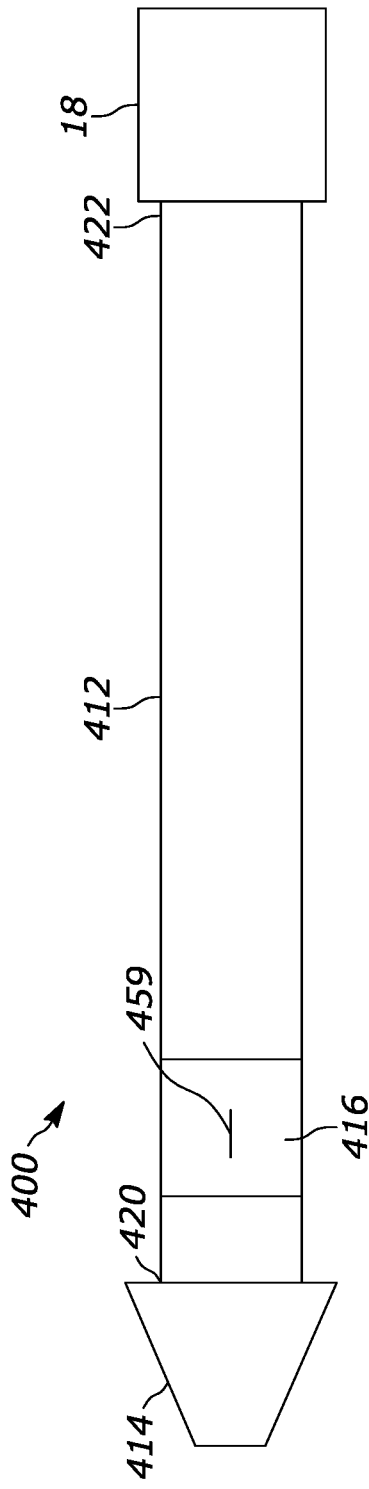
FIG. 17 of the drawings is a schematic view of another configuration of a self-intermittent urinary catheter extension of the present disclosure.
Figure 18:
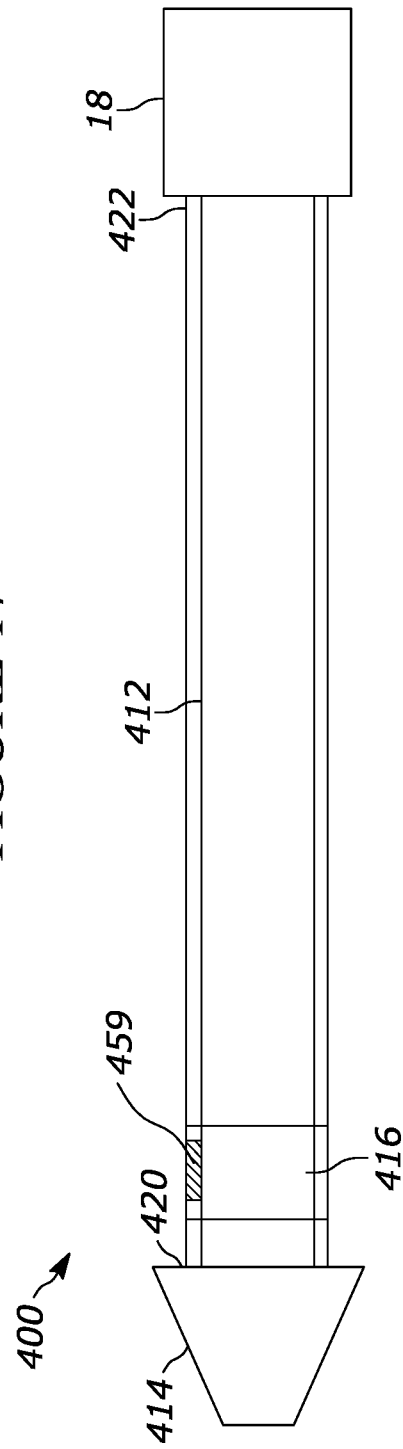
FIG. 18 of the drawings is a schematic cut view of the self-intermittent urinary catheter extension shown in FIG. 17.

With references to FIGS. 17 and 18, another configuration of a self-intermittent urinary catheter extension is disclosed, shown generally at 400. The catheter extension 400 is shown as comprising an extension tube 412, and in at least one configuration a catheter connector or extension connector 414 and the bag coupling connector 18. The extension tube 412, similar to the extension tube 12 discussed above, is shown as comprising a tubular member formed from a polymer, such as a latex free polymer. In many configurations, the tubular member may be clear and transparent, while in other configurations, the tubular member may be translucent or opaque and in varying colors. The extension tube 412 extends between proximal end 420 and distal end 422. The extension tube 412 defines an outer surface 426 and an inner bore 424, which, in the configuration shown, defines a substantially uniform cylindrical configuration with a substantially uniform wall thickness. Of course, variations are contemplated in the configuration and cross-sectional shape of the extension tube. The catheter extension 400 can be used with the catheter tube 301, discussed above.

Coupled to the proximal end 420 of the extension tube 412 is the extension connector 414, such as an extension connector. In this configuration, the extension connector 414 is a typical catheter connector that is used with typical self-intermittent urinary catheter extension assembly. As such, the details of which are known to those skilled in the art and will not be explained in detail herein for brevity. In at least one configuration, coupled to the distal end 422 of the extension tube 412 is the bag coupling connector 18, as discussed above.

In this configuration, instead of utilizing the radial passage 59 disposed through the body 30 of the extension connector 14 as discussed above, the catheter extension 400 utilizes an opening, such as a slotted passage 459 (e.g., circular, oval, square, or another other shape) that is disposed through the extension tube 412. Although the slotted passage 459 can be disposed anywhere between the proximal end 420 and the distal end 422 of the extension tube 412, in at least one configuration the slotted passage 459 is disposed proximate to the proximal end 420 of the extension tube 412. The slotted passage 459 is shown in FIG. 18 as comprising a passage that includes inner end 472 and outer end 474. A length of the slotted passage 459 extends along a length of the extension tube 412, as shown. The slotted passage 459 places the interior of the extension tube 412 in fluid communication with an exterior of the extension tube 412.

Figure 19:
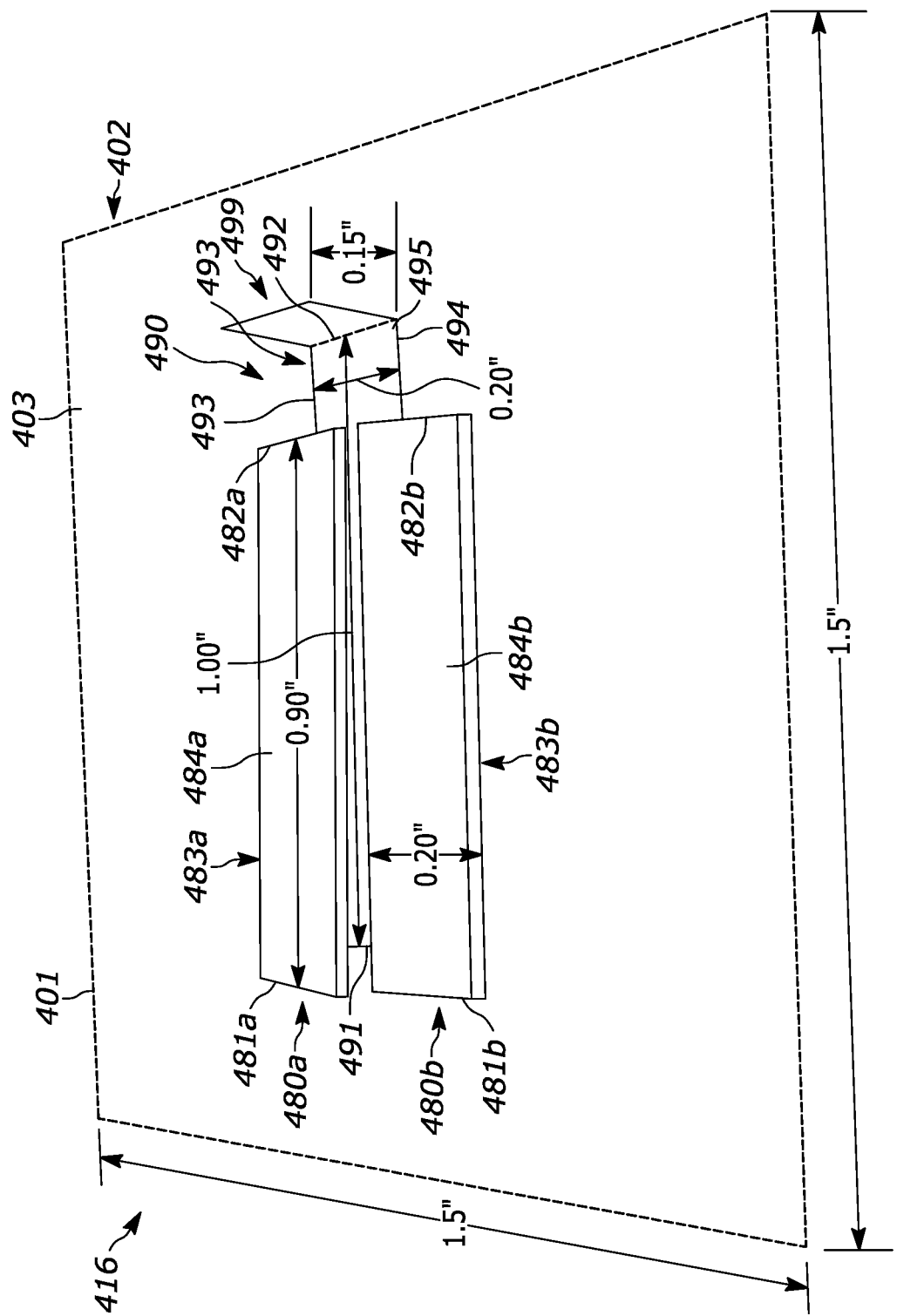
FIG. 19 of the drawings is an isometric view of another configuration of an indicator assembly.

With reference to FIG. 19, a detailed view of another configuration of an indicator assembly is shown, indicator assembly 416. In at least one configuration, the indicator assembly 416 is comprised of a sealing member 401, a wicking member 490, a first indicator 480a, and a second indicator 480b. However, one skilled in the art would appreciate that the indicator assembly 416 can include one of the two indicators shown, dependent upon what is being tested for. As UTIs result in trace amount of Nitrite and Leukocyte being present in urine, one of the first and second indicators 480a, 480b can be used to detect Nitrite and another of the first and second indicators 480a, 480b can be used to detect Leukocyte. In other configurations, the indicator assembly 416 can be used to test for other chemicals within urine.

The sealing member 401 is at least partially a clear sealing film that allows visual inspection of the first and second indicators 480a, 480b once the indicator assembly 416 is disposed onto the extension tube 412. In at least one configuration, the sealing member 401 is square in shape, as shown, although other shapes are possible such as rectangular, circular, oval, or any other shape. In at least one configuration, the sealing member 401 is approximately 1.5" in width×1.5" in height. The sealing member 401 is comprised of a first side 402 and a second side 403 that is coupled to the extension tube 412.

The sealing member 401 seals the wicking member 490 and the first and second indicators 480a, 480b against the extension tube 412 such that during use urine does not leak from the sealing member 401. The sealing member 401 can be a clear plastic tape material that is used to adhesively couple the wicking member 490 and the first and second indicators 480a, 480b against the extension tube 412. In another configuration, the sealing member 401 can be a clear shrink wrap material that shrinks when exposed to heat to mechanically couple the wicking member 490 and the first and second indicators 480a, 480b against the extension tube 412, or any other type of member that couples the wicking member 490 and the first and second indicators 480a, 480b against the extension tube 412.

The wicking member 490 has the same operating properties as the wicking member 90, but in this configuration is a rectangular shaped member to transport urine along a length of the first and second indicators 480a, 480b, although other shapes are possible. The wicking member 490 is comprised of a first end 491, a second end 492, a first side 493, and a second side 494. In at least one configuration, the wicking member 490 is 1.00" in width from the first end 491 to the second end 492, and 0.20" in height. In the configuration shown, the first end 491 of the wicking member 490 is closer to a center of the sealing member 401 such that the first end 491 of the wicking member 490 does not align with first ends 481a, 481b of the first and second indicators 480a, 480b. The wicking member 490 further comprises a first side 495 and a second side 496, the first side 495 being disposed against the second side 403 of the sealing member 401. The wicking member 490 is comprised of a wicking tab 499 that can be disposed at the second end 492 of the wicking member 490, the wicking tab 499 not coupled to the sealing member 401. In at least one configuration, the wicking tab 499 can be 0.15" in width and a same height as the wicking member 490, this being rectangular in shape. In other configurations, the wicking tab 499 can be circular in cross section similar to a candle wick, square, triangular, a semi-circle, or another other shape that allows for wicking.

Figure 20:
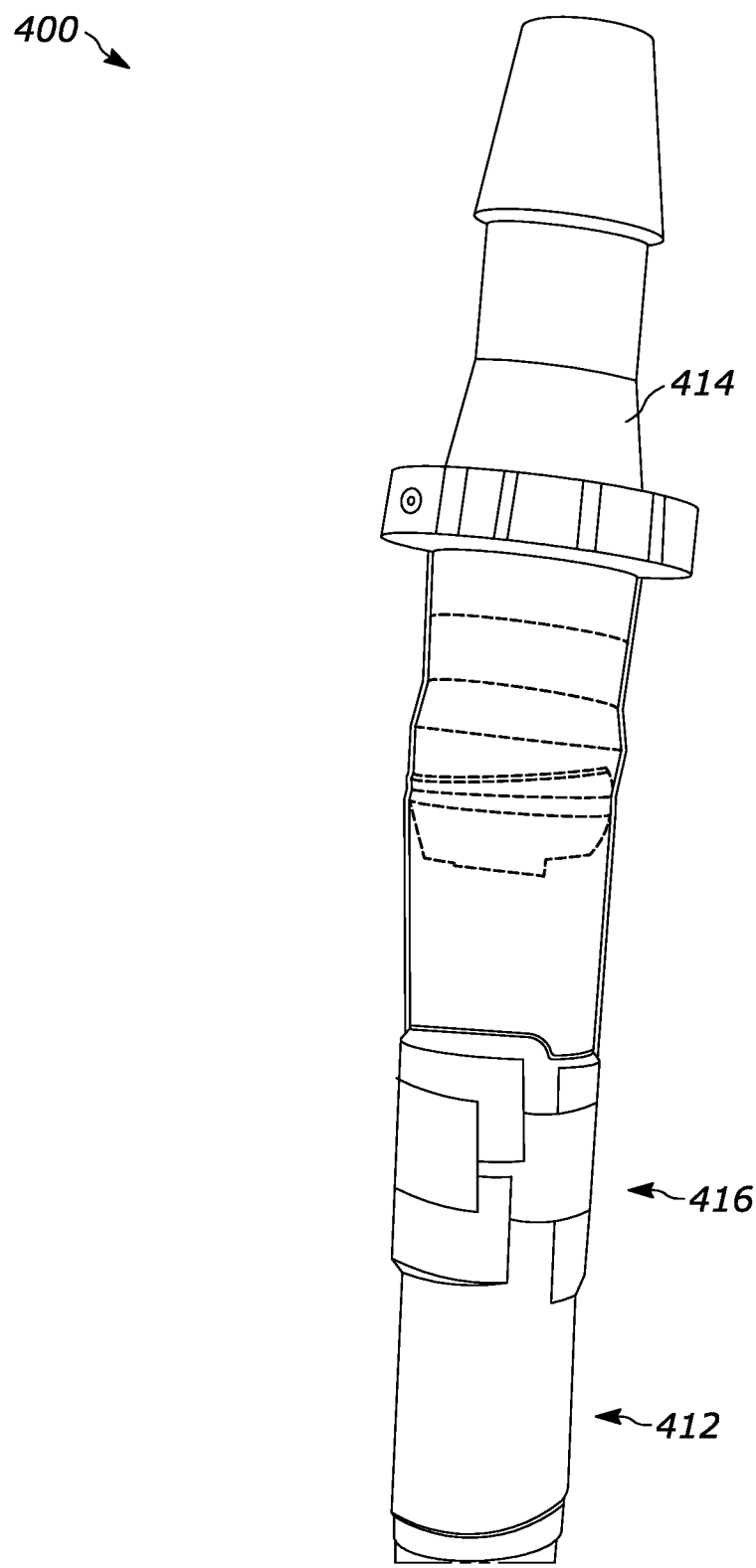
FIG. 20 of the drawings is a side view of the indicator assembly coupled to an extension tube.
Figure 21:
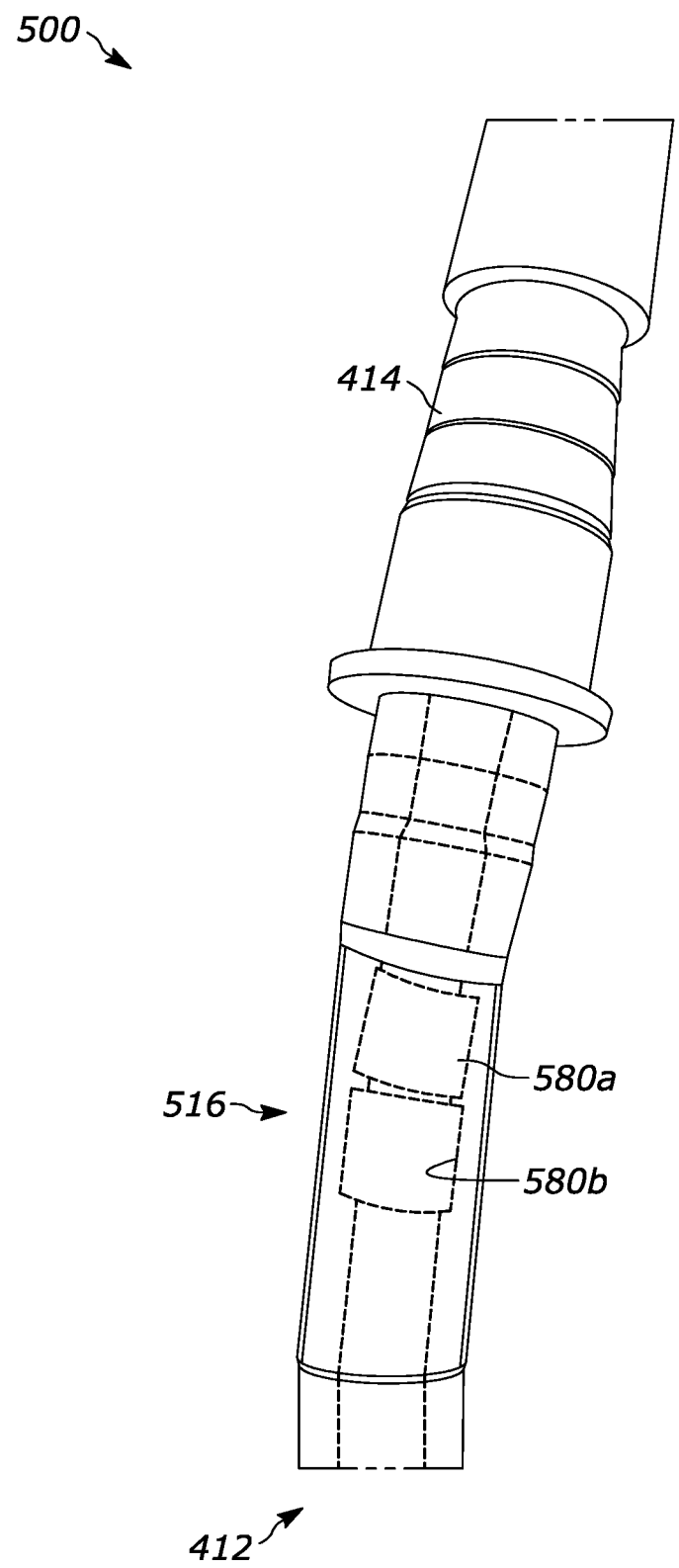
FIG. 21 of the drawings is a side view of another configuration of the indicator assembly coupled to an extension tube.

The first and second indicators 480a, 480b further comprise second ends 482a, 482b on opposite ends of the first and second indicators 480a, 480b from the first ends 481a, 481b, respectively. In at least one configuration, the first and second indicators 480a, 480b are approximately same in dimensions, such as 0.90" in width and 0.20" in height to allow the first and second indicators 480a, 480b to wrap substantially around the extension tube 412, as shown in FIG. 20. In at least one other configuration, another catheter extension, catheter extension 500 can include an indicator assembly 516 that is comprised of first and second indicators 580a, 580b that are approximately square in shape with, as shown in FIG. 21. The first and second indicators 480a, 480b each include a first side 483a, 483b and a second side 484a, 484b. Although the first and second indicators 480a, 480b can be otherwise disposed, in at least one configuration, approximately half of the height of the first sides 483a, 483b of the first and second indicators 480a, 480b is disposed against the second side 496 of the wicking member 490, and approximately half of the height of the first sides 483a, 483b of the first and second indicators 480a, 480b is disposed on the second side 403 of the sealing member 401, such that the first and second indicators 480a, 480b are in fluid communication with the wicking member 490. This overlap in heights allows fluid to be conducted from the wicking member 490 to the first and second indicators 480a, 480b.

Figure 22:
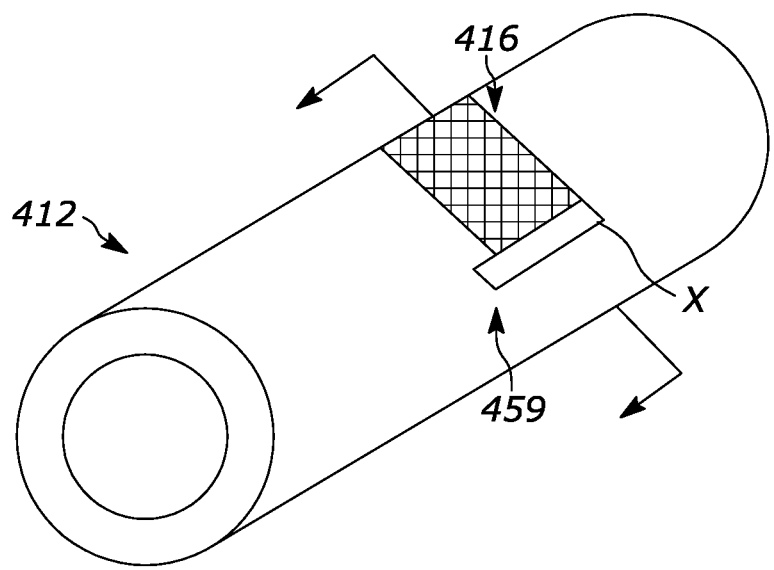
FIG. 22 of the drawings is a schematic view of the indicator assembly coupled to the extension tube.
Figure 23:
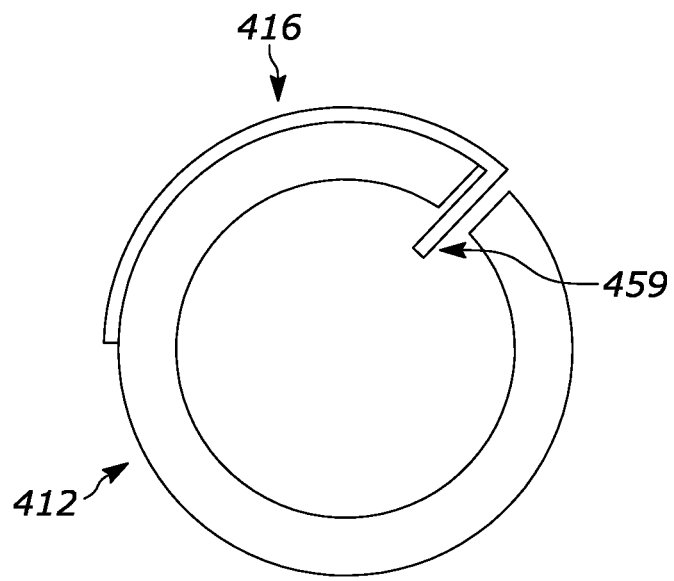
FIG. 23 of the drawings is a side view of FIG. 22 showing a wicking tab extending into an interior of the extension tube.

During assembly of the indicator assembly 416, the indicator assembly 416 is positioned over the extension tube 412 such that the height of the wicking tab 419 is aligned with the length of the slotted passage 459, as shown in FIG. 22. The wicking tab 499 is then disposed within the slotted passage 459 such that the wicking tab 499 extends into an interior of the extension tube 412, shown in FIG. 23. Then, the indicator assembly 416 is coupled to the extension tube 412, thereby sealing the slotted passage 459 so that the urine cannot escape from the interior of the extension tube 412. Once so disposed, the wicking tab 499 absorbs urine as it traverses the extension tube 412 and transports a small quantity of the urine through the slotted passage 459 to the first and second indicators 480a, 480b.

The foregoing description merely explains and illustrates the disclosure and the disclosure is not limited thereto except insofar as the appended claims are so limited, as those skilled in the art who have the disclosure before them will be able to make modifications without departing from the scope of the disclosure.

What is claimed is:

1. An extension assembly for a catheter, the extension assembly comprising:
   an extension connector having a body with a central bore, the extension connector further including:
   a tube coupling assembly structurally configured to be attachable to an extension tube;
   a catheter coupling assembly structurally configured to be attachable to a catheter;
   a central test portion positioned between the tube coupling and the catheter coupling, the central test portion comprising:
   a lower end wall extending between the tube coupling and the catheter coupling;
   a cover member extending over the lower end wall between the tube coupling and the catheter coupling, the lower end wall and the cover member defining at least one slot therebetween;
   at least one radial passage extending from the central bore to the at least one slot placing the central bore and the at least one slot in fluid communication; and
   at least one wicking member comprising an elongated rectangular member having a bend, defining a flow contact portion, the flow contact portion extendable through the at least one radial passage so as to have an end thereof exposed to the central bore, with a remaining portion being positioned within the slot, along at least one of the lower end wall and the cover member, at least a portion positioned within the slot structurally configured to change color in a presence of a chemical indicative of a bladder infection, the at least one wicking member being structurally configured to draw a liquid thereinto by capillary action into the slot.

2. The extension assembly of claim 1 wherein:
the at least one radial passage comprises a pair of radial passages extending from the central bore to the at least one slot;
the at least one wicking member associated with each of the pair of radial passages.

3. The extension assembly of claim 1 wherein the at least one slot comprises a substantially rectangular lower end wall.

4. The extension assembly of claim 1, wherein the at least one radial passage comprises a rectangular cross-sectional configuration.

5. The extension assembly of claim 1 wherein the at least one wicking member includes a first portion and a second portion, wherein the second portion is substantially perpendicular to the first portion.

6. The extension assembly of claim 1 wherein the cover member comprises a transparent member.

7. The extension assembly of claim 1 wherein the extension connector comprises a polymer member.

8. The extension assembly of claim 1 further comprising:
an extension tube having a proximal end and a distal end, the extension tube having an inner bore, the proximal end of the extension tube coupled to the first end of the body.

9. The extension assembly of claim 1 wherein the catheter coupling assembly includes an outer surface, wherein the outer surface has a reducing cross-sectional area toward a distal end thereof.

10. The extension assembly of claim 1 wherein a cross-sectional area of the tube coupling assembly is smaller than a cross-sectional area of the catheter coupling assembly.

11. A method of using an extension assembly of claim 1 comprising the steps of:
passing urine through the central bore;
allowing a portion of urine to contact the at least one wicking member;
wicking urine through the at least one radial passage;
wicking urine into the slot;
allowing the at least one wicking member to be in contact with urine, sufficient to allow for a color change if there is a chemical in the urine indicative of a bladder infection; and
changing color of the at least one wicking member if there is a chemical in the urine indicative of a bladder infection.

12. The method according to claim 11 further comprising the step of:
attaching the extension assembly to the catheter prior to the step of passing urine through the central bore; and
passing urine through the catheter prior to the step of passing urine through the central bore.

13. The method according to claim 11 further comprising the step of:
attaching a hose to the extension assembly opposite the catheter prior to the step of passing urine through the central bore and prior to the step of passing urine through the catheter.

14. The method of claim 11 further comprising the step of:
viewing the at least one wicking member; and
determining if the at least one wicking member changed color so as to be indicative of a bladder infection.

* * * * *